US011103177B2

(12) United States Patent
Relan

(10) Patent No.: US 11,103,177 B2
(45) Date of Patent: *Aug. 31, 2021

(54) SYSTEM AND METHOD FOR MAPPING CARDIAC ACTIVITY

(71) Applicant: St. Jude Medical, Cardiology Division, Inc., St. Paul, MN (US)

(72) Inventor: Jatin Surendra Relan, Bordeaux (FR)

(73) Assignee: St, Jude Medical, Cardiology Division, Inc., St. Paul, MN (US)

( * ) Notice: Subject to any disclaimer, the term of this patent is extended or adjusted under 35 U.S.C. 154(b) by 84 days.

This patent is subject to a terminal disclaimer.

(21) Appl. No.: 16/294,313

(22) Filed: Mar. 6, 2019

(65) Prior Publication Data

US 2019/0320927 A1 Oct. 24, 2019

Related U.S. Application Data

(60) Provisional application No. 62/659,406, filed on Apr. 18, 2018.

(51) Int. Cl.
*A61B 5/366* (2021.01)
*A61B 5/0245* (2006.01)
*A61B 5/00* (2006.01)
*A61B 5/339* (2021.01)

(52) U.S. Cl.
CPC ............ *A61B 5/366* (2021.01); *A61B 5/0245* (2013.01); *A61B 5/339* (2021.01); *A61B 5/726* (2013.01)

(58) Field of Classification Search
CPC ...... A61B 5/0472; A61B 5/044; A61B 5/0245; A61B 5/726; A61B 5/7253; A61B 5/7264; A61B 5/0422; A61B 5/366; A61B 5/339; A61B 5/287
See application file for complete search history.

(56) References Cited

U.S. PATENT DOCUMENTS

| | | | |
|---|---|---|---|
| 5,697,377 | A | 12/1997 | Wittkampf |
| 5,983,126 | A | 1/1999 | Wittkampf |
| 6,640,119 | B1 | 10/2003 | Budd et al. |
| 6,728,562 | B1 | 4/2004 | Budd et al. |
| 6,939,309 | B1 | 9/2005 | Beatty et al. |
| 6,947,785 | B1 | 9/2005 | Beatty et al. |
| 6,978,168 | B2 | 12/2005 | Beatty et al. |
| 6,990,370 | B1 | 1/2006 | Beatty et al. |
| 7,263,397 | B2 | 8/2007 | Hauck et al. |
| 7,885,707 | B2 | 2/2011 | Hauck |

(Continued)

*Primary Examiner* — Gary Jackson
*Assistant Examiner* — Sebastian X Lukjan
(74) *Attorney, Agent, or Firm* — Wiley Rein LLP

(57) ABSTRACT

QRS activity duration may be indicative of cardiac tissue health. Accordingly, maps of QRS activity duration may be beneficial to practitioners. To this end, an electroanatomical mapping system can receive an electrogram signal and analyze it by transforming it into the wavelet domain, computing an energy function of the resultant scalogram, and computing QRS activity duration using the energy function. A graphical representation of the QRS activity duration can be output, for example on a three-dimensional cardiac model. Areas of diseased substrate can be identified on the output; in some aspects of the disclosure, diseased substrate corresponds to areas where the QRS activity duration exceeds a preset threshold, such as about 70 ms.

15 Claims, 6 Drawing Sheets

(56) References Cited

U.S. PATENT DOCUMENTS

| | | | |
|---|---|---|---|
| 2010/0014723 A1* | 1/2010 | Addison | A61B 5/726 382/128 |
| 2012/0197148 A1* | 8/2012 | Levitan | A61B 5/0452 600/515 |
| 2014/0213862 A1* | 7/2014 | Addison | A61B 5/02116 600/324 |
| 2015/0208942 A1* | 7/2015 | Bar-Tai | A61B 5/0422 600/374 |
| 2017/0086693 A1* | 3/2017 | Peterson | A61B 5/0456 |
| 2019/0038165 A1 | 2/2019 | Relan et al. | |

* cited by examiner

SYSTEM AND METHOD FOR MAPPING CARDIAC ACTIVITY

CROSS-REFERENCE TO RELATED APPLICATIONS

This application claims the benefit of U.S. provisional application No. 62/659,406, filed 18 Apr. 2018, which is hereby incorporated by reference as though fully set forth herein.

BACKGROUND

The present disclosure relates generally to electrophysiological mapping, such as may be performed in cardiac diagnostic and therapeutic procedures. In particular, the present disclosure relates to systems, apparatuses, and methods for mapping diseased cardiac substrate.

It is known to use the peak-to-peak voltage of an intracardiac electrogram to evaluate the atrial substrate of an atrial fibrillation patient in sinus rhythm. It is hypothesized, however, that QRS activity duration may also be informative when attempting to identify diseased substrate in an atrial fibrillation patient in sinus rhythm.

BRIEF SUMMARY

Disclosed herein is a method of mapping cardiac activity, including receiving an electrogram signal S(t) at a signal processor; and, using the signal processor: transforming the electrogram signal S(t) into the wavelet domain, thereby computing a scalogram G(f, t); computing an energy function L(t) of the scalogram G(f, t); and computing a QRS activity duration for the electrogram signal S(t) using the energy function L(t).

The step of transforming the electrogram signal S(t) into the wavelet domain can include applying a continuous wavelet transformation to the electrogram signal S(t) to compute the scalogram G(f, t). The continuous wavelet transformation can utilize a high time-resolution mother wavelet, such as a Paul wavelet, when a peak-to-peak voltage of the electrogram signal S(t) does not exceed a preset threshold (e.g., about 3 mV), and can utilize a high frequency-resolution mother wavelet, such as a Morlet wavelet, when the peak-to-peak voltage exceeds the preset threshold.

The step of computing an energy function L(t) of the scalogram G(f, t) can include: detecting a time $T^{max}$ at which G(f, t) reaches a maximum; detecting a time $T^{down}$ prior to $T^{max}$ at which G(f, t) first drops below a preset noise threshold; detecting a time $T^{up}$ after $T^{max}$ at which G(f, t) first drops below the preset noise threshold: and computing the energy function L(t) according to an equation $$L(t) = \begin{cases} \max(G(f,t)), & \text{if } T^{down} \leq t \leq T^{up} \\ 0, & \text{elsewhere} \end{cases},$$

where f is between 0 Hz and 1000 Hz. The preset noise threshold in normalized scale can be about 0.3 when the transforming step utilizes a high time-resolution mother wavelet and about 0.45 otherwise.

The step of computing a QRS activity duration for the electrogram signal S(t) using the energy function L(t) can include: computing a pulse wave $L^{Pulse}(t)$ having a pulse duration according to an equation $$L^{Pulse}(t) = \begin{cases} 1, & \text{if } L(t) > 0 \\ 0, & \text{otherwise} \end{cases};$$

and defining the QRS activity duration for the electrogram signal S(t) to be equal to the pulse duration.

In aspects of the disclosure, the method also includes generating a graphical representation of a plurality of QRS activity durations for a plurality of electrogram signals S(t) on a three-dimensional cardiac model. Optionally, one or more areas of diseased substrate, characterized by QRS activity durations in excess of a preset threshold (e.g., about 70 ms) can be identified on the three-dimensional cardiac model.

The instant disclosure also provides a method of mapping cardiac substrate, including receiving an electrophysiology data point having an associated electrogram signal at an electroanatomical mapping system and, using the electroanatomical mapping system: transforming the electrogram signal into the wavelet domain; and computing a QRS activity duration for the electrogram signal in the wavelet domain. These steps can be repeated for a plurality of electrophysiology data points, thereby creating a QRS activity duration map, a graphical representation of which can be output on a three-dimensional cardiac model.

The step of transforming the electrogram signal into the wavelet domain can include applying a continuous wavelet transform to the electrogram signal. The continuous wavelet transform can utilize a high time-resolution mother wavelet when a peak-to-peak voltage of the electrogram signal does not exceed a preset threshold and a high frequency-resolution mother wavelet when the peak-to-peak voltage exceeds the preset threshold.

According to embodiments disclosed herein, the method also includes classifying the electrophysiology data point as a diseased substrate point if the computed QRS activity duration exceeds a preset threshold, such as about 70 ms.

Also disclosed herein is an electroanatomical mapping system, including a wavelet transformation processor configured to: receive an electrophysiology data point having an associated electrogram signal; transform the electrogram signal into the wavelet domain; and compute a QRS activity duration for the electrogram signal in the wavelet domain, as well as a mapping processor configured to generate a QRS activity map from a plurality of QRS activity durations computed by the wavelet transformation processor. The mapping processor can also be configured to output a graphical representation of the QRS activity map on a three-dimensional cardiac model.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The instant disclosure provides systems, apparatuses, and methods for the creation of electrophysiology maps (e.g., electrocardiographic maps) that provide information regarding cardiac activity. Certain embodiments of the disclosure will be explained with reference to the use of bipolar electrograms to create electrophysiology maps, and in particular to create maps of QRS duration. The teachings herein can be applied to good advantage in evaluating the atrial substrate during sinus rhythm in atrial fibrillation patients, and can facilitate identification of diseased substrate.

For purposes of illustration, aspects of the disclosure will be described in detail herein in the context of a cardiac mapping procedure carried out using an electrophysiology mapping system (e.g., using an electroanatomical mapping system such as the EnSite Precision™ cardiac mapping system from Abbott Laboratories).

Figure 1:
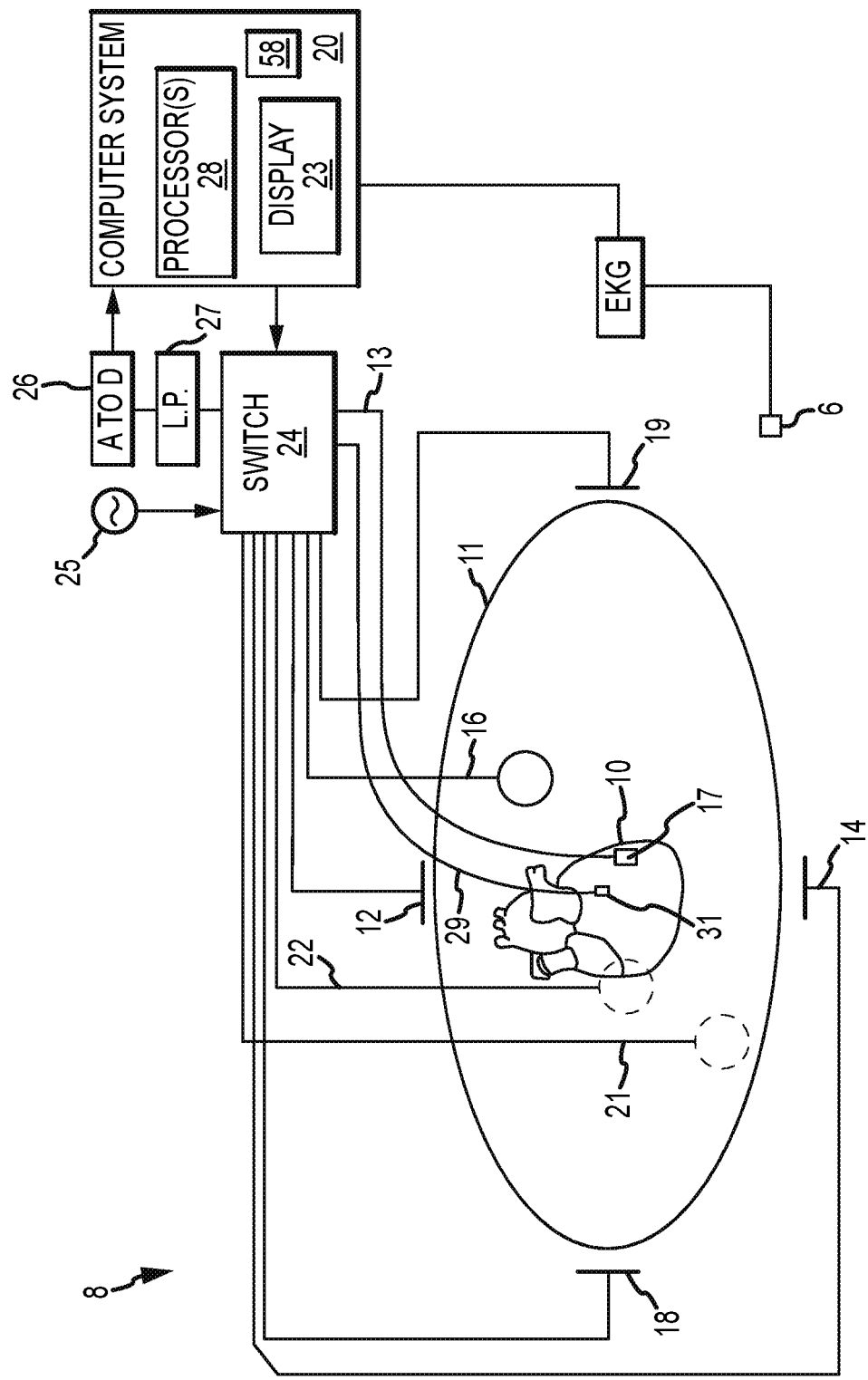
FIG. 1 is a schematic diagram of an exemplary electroanatomical mapping system.

FIG. 1 shows a schematic diagram of an exemplary electroanatomical mapping system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10.

As one of ordinary skill in the art will recognize, and as will be further described below, system 8 determines the location, and in some aspects the orientation, of objects, typically within a three-dimensional space, and expresses those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only a single lead 6 and its connection to computer 20 is illustrated in FIG. 1.

A representative catheter 13 having at least one electrode 17 is also shown. This representative catheter electrode 17 is referred to as the "roving electrode," "moving electrode," or "measurement electrode" throughout the specification. Typically, multiple electrodes 17 on catheter 13, or on multiple such catheters, will be used. In one embodiment, for example, the system 8 may comprise sixty-four electrodes on twelve catheters disposed within the heart and/or vasculature of the patient. In other embodiments, system 8 may utilize a single catheter that includes multiple (e.g., eight) splines, each of which in turn includes multiple (e.g., eight) electrodes.

The foregoing embodiments are merely exemplary, however, and any number of electrodes and/or catheters may be used. For example, in some embodiments, a high density mapping catheter, such as the Ensite™ Array™ non-contact mapping catheter of Abbott Laboratories, can be utilized.

Figure 2:
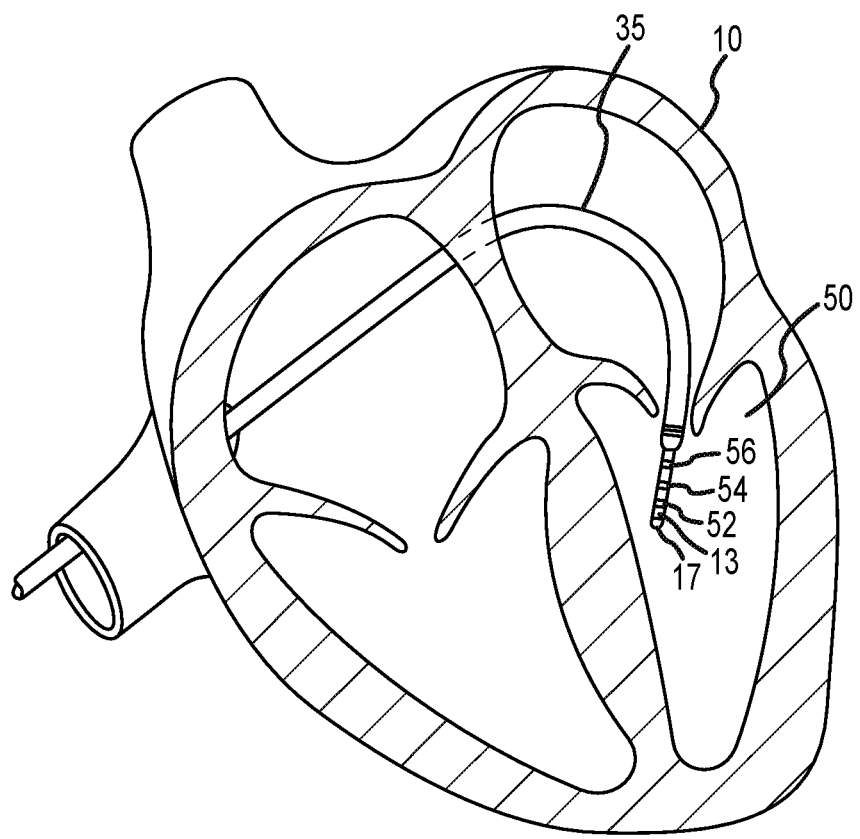
FIG. 2 depicts an exemplary catheter that can be used in connection with aspects of the instant disclosure.

Likewise, it should be understood that catheter 13 (or multiple such catheters) are typically introduced into the heart and/or vasculature of the patient via one or more introducers and using familiar procedures. For purposes of this disclosure, a segment of an exemplary catheter 13 is shown in FIG. 2. In FIG. 2, catheter 13 extends into the left ventricle 50 of the patient's heart 10 through a transseptal sheath 35. The use of a transseptal approach to the left ventricle is well known and will be familiar to those of ordinary skill in the art, and need not be further described herein. Of course, catheter 13 can also be introduced into the heart in any other suitable manner.

Catheter 13 includes electrode 17 on its distal tip, as well as a plurality of additional measurement electrodes 52, 54, 56 spaced along its length in the illustrated embodiment. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by system 8.

Similarly, each of electrodes 17, 52, 54, and 56 can be used to gather electrophysiological data from the cardiac surface (e.g., surface electrograms). The ordinarily skilled artisan will be familiar with various modalities for the acquisition and processing of electrophysiology data points (including, for example, both contact and non-contact electrophysiological mapping), such that further discussion thereof is not necessary to the understanding of the techniques disclosed herein. Likewise, various techniques familiar in the art can be used to generate a graphical representation of a cardiac geometry and/or of cardiac electrical activity from the plurality of electrophysiology data points. Moreover, insofar as the ordinarily skilled artisan will appreciate how to create electrophysiology maps from electrophysiology data points, the aspects thereof will only be described herein to the extent necessary to understand the present disclosure.

Returning now to FIG. 1, in some embodiments, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20 may comprise, for example, a conventional general-purpose computer, a special-purpose computer, a distributed computer, or any other type of computer. The computer 20 may comprise one or more processors 28, such as a single central processing unit ("CPU"), or a plurality of processing units, commonly referred to as a parallel processing environment, which may execute instructions to practice the various aspects described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17 placed in the heart 10 are exposed to the field from a current pulse and are measured with respect to ground, such as belly patch 21. In practice the catheters within the heart 10 may contain more or fewer electrodes than the sixteen shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which system 8 measures positions. Data sets from each of the surface electrodes, the internal electrodes, and the virtual electrodes may all be used to determine the location of the roving electrodes 17 within heart 10.

The measured voltages may be used by system 8 to determine the location in three-dimensional space of the electrodes inside the heart, such as roving electrodes 17 relative to a reference location, such as reference electrode 31. That is, the voltages measured at reference electrode 31 may be used to define the origin of a coordinate system, while the voltages measured at roving electrodes 17 may be used to express the location of roving electrodes 17 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described, for example, in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

Therefore, in one representative embodiment, system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ or EnSite Precision™ cardiac mapping and visualization system of Abbott Laboratories. Other localization systems, however, may be used in connection with the present teachings, including for example the RHYTHMIA HDX™ mapping system of Boston Scientific Corporation, the CARTO navigation and location system of Biosense Webster, Inc., the AURORA® system of Northern Digital Inc., Sterotaxis' NIOBE® Magnetic Navigation System, as well as MediGuide™ Technology from Abbott Laboratories.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

Figure 3:
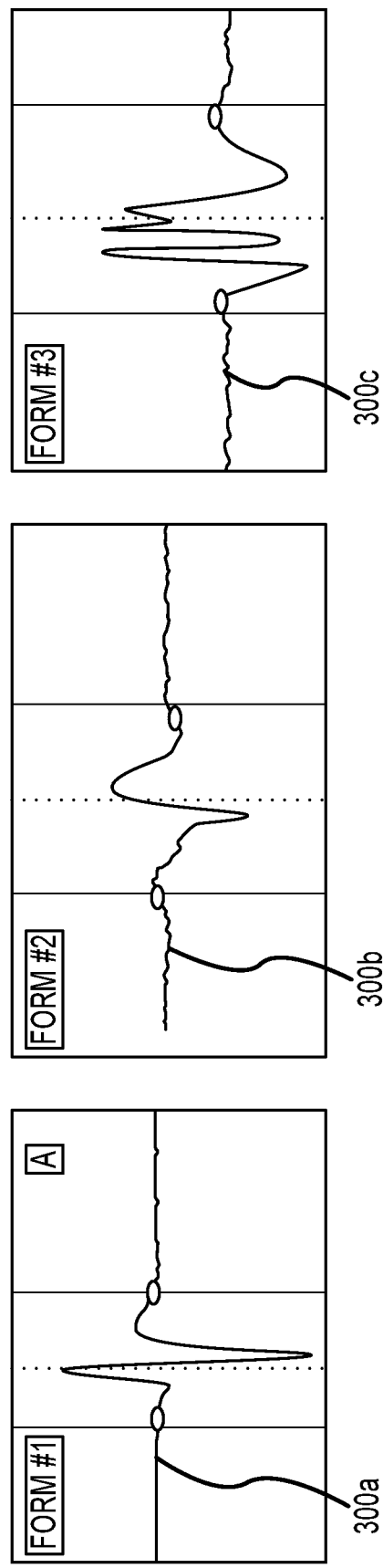
FIGS. 3A through 3C are representative electrogram signals.

Aspects of the disclosure relate to mapping QRS duration. In particular, when mapping within and around an atrial substrate in an atrial fibrillation patient, intracardiac bipolar electrograms can take one of several forms: a single component QRS activity lasting for a short duration, shown as trace 300a in FIG. 3A; a single component QRS activity lasting for a long duration, shown as trace 300b in FIG. 3B; or a multiple component (that is, fractionated) QRS activity lasting for a long duration, shown as trace 300c in FIG. 3C.

For purposes of this disclosure, "short duration" QRS activity indicates fast wave conduction within the underlying tissue, which can be presumed to be healthy. On the other hand, "long duration" QRS activity indicates slow wave conduction or block within the underlying tissue, and thus can be presumed to be diseased. Suitable quantitative distinctions between "short duration" and "long duration" QRS activity are described in greater detail below.

Accordingly, system 8 can also include a QRS detection module 58. QRS detection module 58 can be used, inter alia, to measure QRS duration, as discussed in detail below. In turn, the long duration signals, whether single component or multiple component, may be indicative of diseased substrate, allowing a practitioner to identify additional potential therapy (e.g., ablation) targets.

Figure 4:
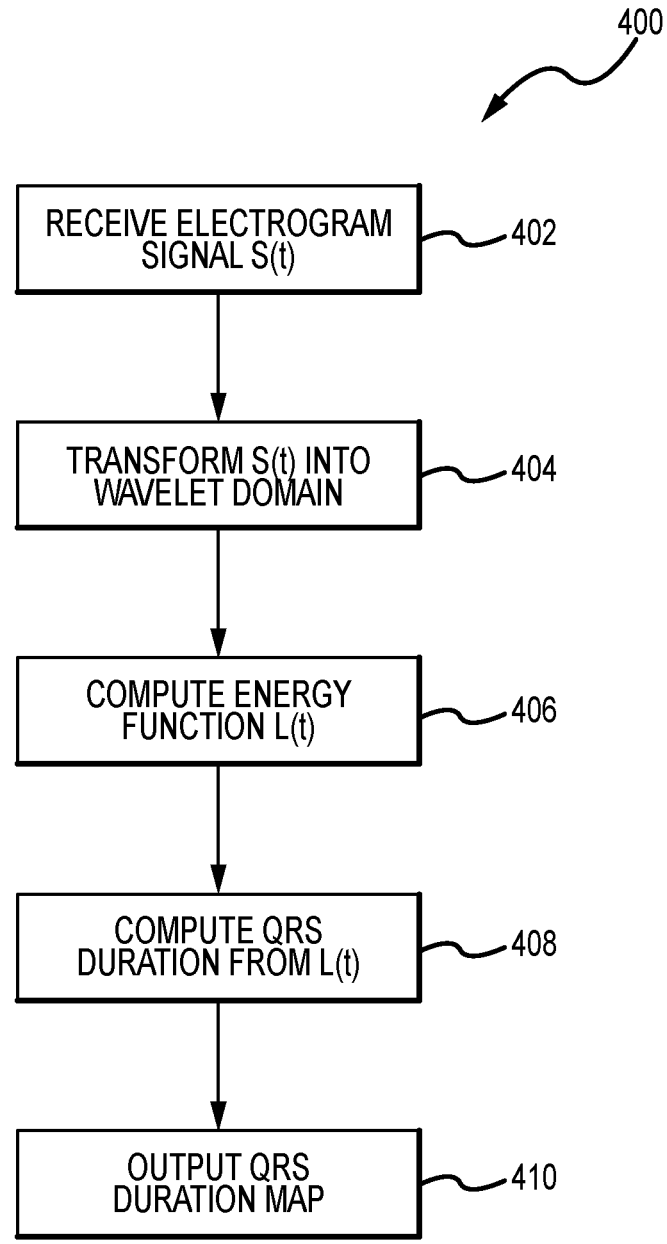
FIG. 4 is a flowchart of representative steps that can be followed according to exemplary embodiments disclosed herein.

One exemplary method of mapping QRS duration according to the present teachings will be explained with reference to the flowchart 400 of representative steps presented as FIG. 4. In some embodiments, for example, flowchart 400 may represent several exemplary steps that can be carried out by electroanatomical mapping system 8 of FIG. 1 (e.g., by processor 28 and/or QRS detection module 58). It should be understood that the representative steps described below can be either hardware- or software-implemented. For the sake of explanation, the term "signal processor" is used herein to describe both hardware- and software-based implementations of the teachings herein.

In block 402, system 8 receives an electrogram signal, denoted S(t), for example in connection with the collection of an electrophysiology data point by catheter 13. According to aspects of the disclosure, the electrogram signal S(t) is a bipolar signal, such as signal 300a, 300b, or 300c.

Figure 5C:
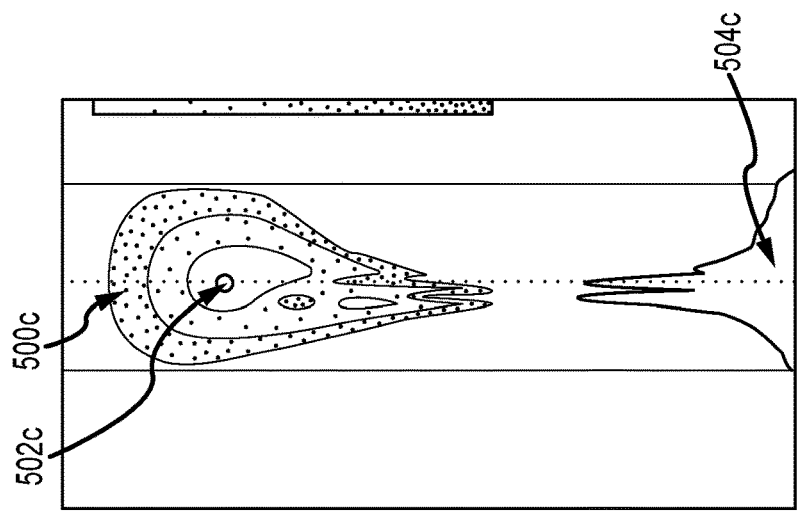
FIGS. 5A through 5C are wavelet domain scalograms and energy functions corresponding, respectively, to the electrogram signals of FIGS. 3A through 3C.
Figure 5B:
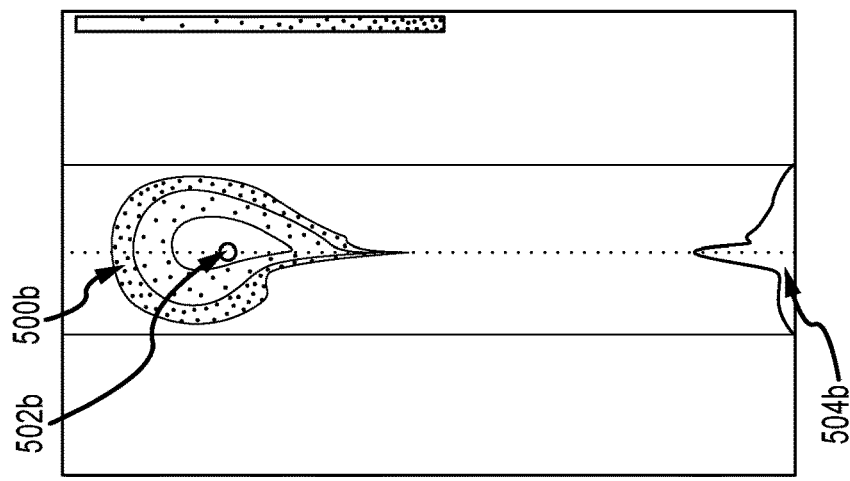
Figure 5A:
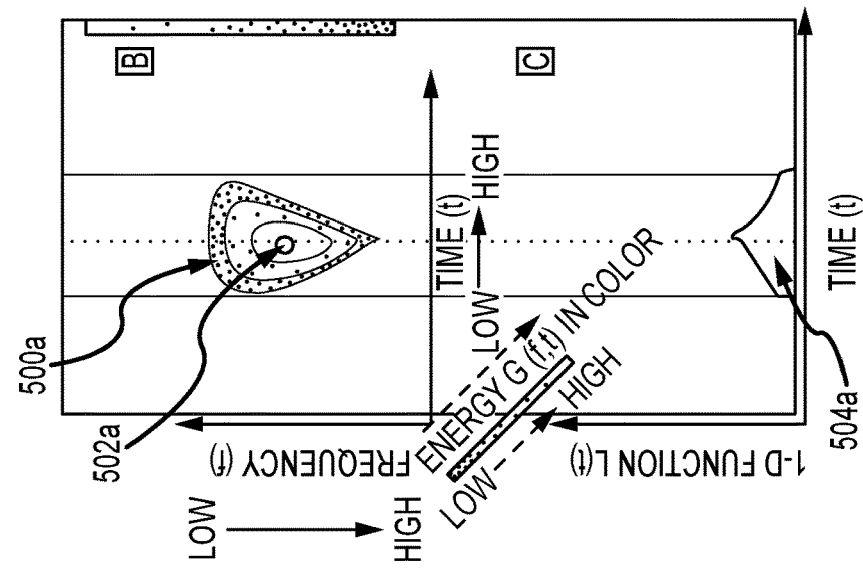

In block 404, the electrogram signal S(t) is transformed into the wavelet domain, which computes a scalogram G(f, t). More specifically, the scalogram G(f, t) can be computed for a preset window, referred to as a "Roving Activation Interval" ("RAI") about a reference time point $T_{ref}$ corresponding to a trigger event (e.g., the signal from an EKG lead). The width of the RAI can be user-defined; in embodiments, the RAI is between about 100 ms and about 300 ms wide. Scalograms 500a, 500b, and 500c, respectively corresponding to electrogram signals 300a, 300b, and 300c, are shown in FIGS. 5A-5C.

In embodiments of the disclosure, block 404 applies a continues wavelet transform to the electrogram signal S(t). The mother wavelet used in the wavelet transform can be a high time-resolution mother wavelet, such as a Paul wavelet, or a high frequency-resolution mother wavelet such as a Morlet wavelet, both of which will be familiar to those of ordinary skill in the art. In particular, it is desirable to use a high time-resolution mother wavelet when a peak-to-peak voltage of electrogram signal S(t) 300a, 300b, 300c does not exceed a preset threshold (e.g., about 3 mV, or another suitable, user-defined threshold value) and to use a high frequency-resolution mother wavelet otherwise.

Other mother wavelets can be employed without departing from the scope of the instant teachings. Likewise, the teachings herein can be applied using discrete, rather than continuous, wavelet transforms.

QRS activity duration for electrogram signal S(t) 300a, 300b, 300c is determined in the wavelet domain. Thus, according to aspects of the disclosure, an energy function L(t) of the scalogram G(f, t) is computed in block 406.

In some embodiments of the disclosure, the energy function L(t) is computed by detecting a time, $T^{max}$, at which G(f, t) reaches a maximum; searching backwards in time from $T^{max}$ to detect a time, $T^{down}$, at which G(f, t) first drops below a preset noise threshold $E^T$; and searching forwards in time from $T^{max}$ to detect a time, $T^{up}$, at which G(f, t) first drops below $E^T$. Referring to FIGS. 5A-5C, $T^{max}$ points 502a, 502b, and 502c are shown in scalograms 500a, 500b, and 500c, respectively. L(t) can then be computed according to an equation $$L(t) = \begin{cases} \max(G(f, t)), & \text{if } T^{down} \leq t \leq T^{up} \\ 0, & \text{elsewhere} \end{cases},$$

where f is between about 0 Hz and about 1000 Hz. The preset noise threshold in normalized scale can be user-defined, and can vary depending on the mother wavelet used. For instance, for a high time-resolution mother wavelet, $E^T$ can be about 0.3, and can be about 0.45 otherwise. Illustrating the foregoing, FIGS. 5A-5C depict energy functions 504a, 504b, and 504c corresponding to scalograms 500a, 500b, and 500c.

In block 408, system 8 computes the QRS duration in the wavelet domain, such as from the energy function L(t). For instance, in aspects of the disclosure, system 8 computes the QRS duration by converting L(t) into a pulse wave $L^{Pulse}(t)$, where $$L^{Pulse}(t) = \begin{cases} 1, & \text{if } L(t) > 0 \\ 0, & \text{otherwise} \end{cases}.$$

The QRS duration can then be defined as the duration of the pulse wave $L^{Pulse}(t)$.

Figure 6:
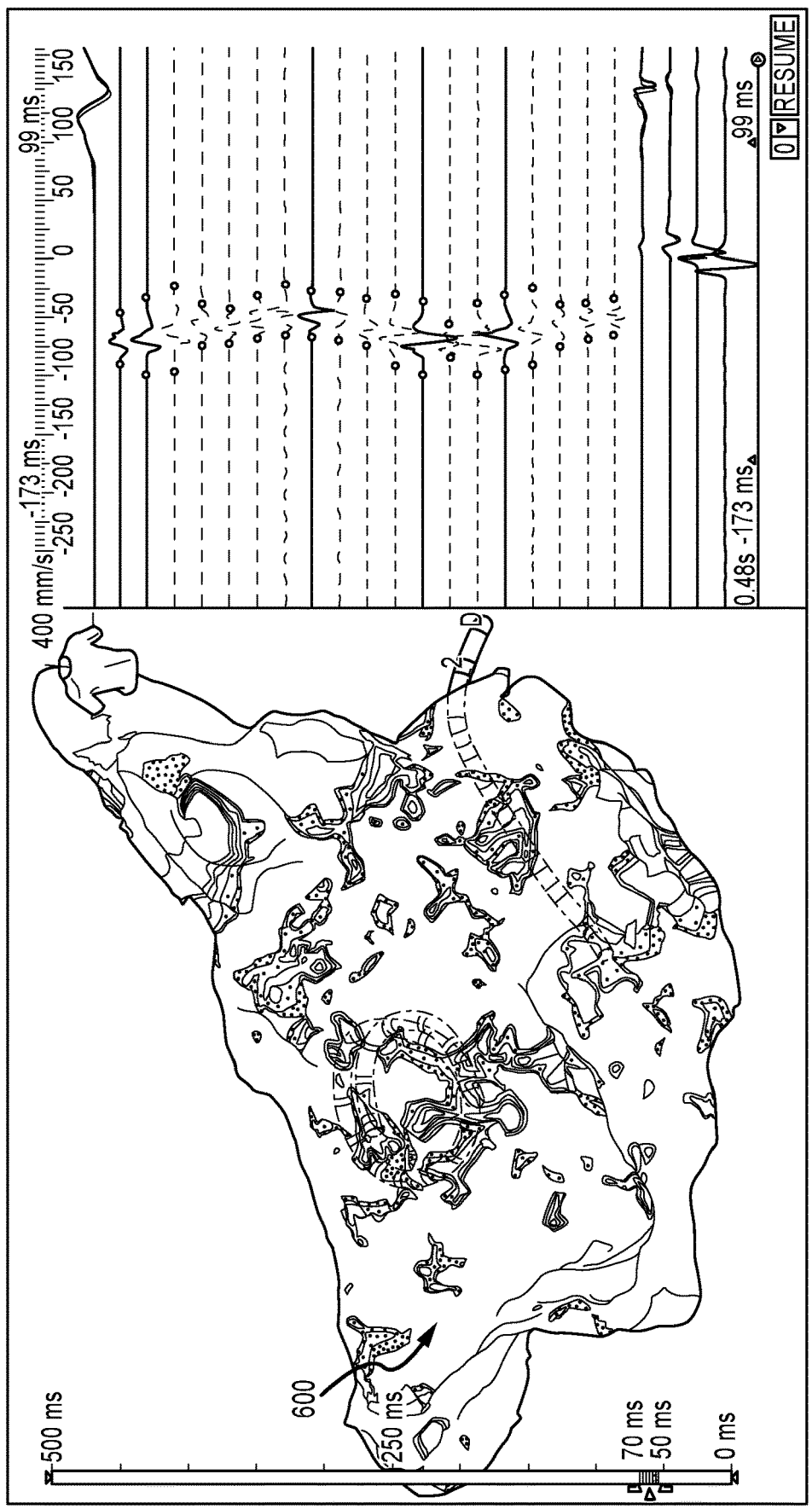
FIG. 6 is a representative graphical representation of a QRS activity duration map, shown on a three-dimensional cardiac model.

Steps 402, 404, 406, and 408 can be repeated for a plurality of electrogram signals S(t), thereby creating a QRS activity duration map. In block 410, the QRS activity duration map can be output, for example on a three-dimensional cardiac model. FIG. 6 is a representative QRS activity duration map on a three-dimensional cardiac model 600.

Optionally, the QRS activity duration map can also be used to identify one or more areas of diseased substrate. In particular, areas of the heart having a QRS activity duration in excess of a preset threshold can be classified as diseased. For instance, areas of the heart having a QRS activity duration in excess of about 70 ms can be classified as scar or diseased tissue; areas of the heart having a QRS activity duration between about 50 ms and about 70 ms can be classified as border zone, and areas of the heart having a QRS activity duration less than about 50 ms can be classified as healthy. Of course, it should be understood that these values can vary with the geometry of catheter 13 (e.g., interelectrode spacing), and thus can be user-defined.

Although several embodiments have been described above with a certain degree of particularity, those skilled in the art could make numerous alterations to the disclosed embodiments without departing from the spirit or scope of this invention.

For example, the teachings herein can be applied in real time (e.g., during an electrophysiology study/as electrophysiology data points are collected) or during post-processing (e.g., to electrophysiology data points collected during an electrophysiology study performed at an earlier time).

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of mapping cardiac activity, comprising:
   receiving an electrogram signal S(t) at a signal processor; and
   using the signal processor:
      transforming the electrogram signal S(t) into the wavelet domain, thereby computing a scalogram G(f, t);
      computing an energy function L(t) of the scalogram G(f, t); and
      computing a QRS activity duration for the electrogram signal S(t) using the energy function L(t), wherein computing a QRS activity duration for the electrogram signal S(t) using the energy function L(t) comprises:
         computing a pulse wave $L^{Pulse}(t)$ according to an equation $$L^{Pulse}(t) = \begin{cases} 1, \text{ if } L(t) > 0 \\ 0, \text{ otherwise} \end{cases},$$

wherein the pulse wave $L^{Pulse}(t)$ has a pulse duration; and
         defining the QRS activity duration for the electrogram signal S(t) to be equal to the pulse duration.

2. The method according to claim 1, wherein transforming the electrogram signal S(t) into the wavelet domain comprises applying a continuous wavelet transformation to the electrogram signal S(t) to compute the scalogram G(f, t).

3. The method according to claim 2, wherein the continuous wavelet transformation utilizes a high time-resolution mother wavelet when a peak-to-peak voltage of the electrogram signal S(t) does not exceed a preset threshold and wherein the continuous wavelet transformation utilizes a high frequency-resolution mother wavelet when the peak-to-peak voltage exceeds the preset threshold.

4. The method according to claim 3, wherein the high time-resolution mother wavelet comprises a Paul wavelet and wherein the high frequency-resolution mother wavelet comprises a Morlet wavelet.

5. The method according to claim 1, wherein computing an energy function L(t) of the scalogram G(f, t) comprises:
   detecting a time $T^{max}$ at which G(f, t) reaches a maximum;
   detecting a time $T^{down}$ prior to $T^{max}$ at which G(f, t) first drops below a preset noise threshold;
   detecting a time $T^{up}$ after $T^{max}$ at which G(f, t) first drops below the preset noise threshold; and
   computing the energy function L(t) according to an equation $$L(t) = \begin{cases} \max(G(f, t)), \text{ if } T^{down} \leq t \leq T^{up} \\ 0, \text{ elsewhere} \end{cases},$$

where f is between 0 Hz and 1000 Hz.

6. The method according to claim 1, further comprising generating a graphical representation of a plurality of QRS activity durations for a plurality of electrogram signals S(t) on a three-dimensional cardiac model.

7. The method according to claim 6, further comprising identifying one or more areas of diseased substrate on the three-dimensional cardiac model, wherein the one or more areas of diseased substrate are characterized by QRS activity durations in excess of a preset threshold.

8. A method of mapping cardiac substrate, comprising:
   receiving an electrophysiology data point having an associated electrogram signal at an electroanatomical mapping system; and
   using the electroanatomical mapping system:
      transforming the electrogram signal into the wavelet domain; and
      computing a QRS activity duration for the electrogram signal in the wavelet domain, wherein computing a QRS activity duration for the electrogram signal in the wavelet domain comprises:
         computing a pulse wave for an energy function of the transformed electrogram signal, wherein the pulse wave has a pulse duration; and
         defining the QRS activity duration for the electrogram signal to be equal to the pulse duration of the pulse wave.

9. The method according to claim 8, further comprising repeating the receiving, transforming, and computing steps for a plurality of electrophysiology data points, thereby creating a QRS activity duration map.

10. The method according to claim 9, further comprising outputting a graphical representation of the QRS activity duration map on a three-dimensional cardiac model.

11. The method according to claim 8, wherein transforming the electrogram signal into the wavelet domain comprises applying a continuous wavelet transform to the electrogram signal.

12. The method according to claim 11, wherein the continuous wavelet transform utilizes a high time-resolution mother wavelet when a peak-to-peak voltage of the electrogram signal does not exceed a preset threshold and wherein the continuous wavelet transformation utilizes a high frequency-resolution mother wavelet when the peak-to-peak voltage exceeds the preset threshold.

13. The method according to claim 8, further comprising classifying the electrophysiology data point as a diseased substrate point if the computed QRS activity duration exceeds a preset threshold.

14. An electroanatomical mapping system, comprising:
   a wavelet transformation processor configured:
      to receive an electrophysiology data point having an associated electrogram signal;
      to transform the electrogram signal into the wavelet domain; and
      to compute a QRS activity duration for the electrogram signal in the wavelet domain by:
         computing a pulse wave for an energy function of the transformed electrogram signal, wherein the pulse wave has a pulse duration; and
         defining the QRS activity duration for the electrogram signal to be equal to the pulse duration; and a mapping processor configured to generate a QRS activity map from a plurality of QRS activity durations computed by the wavelet transformation processor.

15. The system according to claim 14, wherein the mapping processor is further configured to output a graphical representation of the QRS activity map on a three-dimensional cardiac model.

* * * * *